United States Patent
Mollov et al.

(10) Patent No.: US 9,739,735 B2
(45) Date of Patent: Aug. 22, 2017

(54) METHOD AND SYSTEM FOR ON-LINE MONITORING ELECTROLYTIC CAPACITOR CONDITION

(71) Applicant: Mitsubishi Electric Corporation, Tokyo (JP)

(72) Inventors: Stefan Mollov, Rennes (FR); Laurent Foube, Rennes (FR)

(73) Assignee: MITSUBISHI ELECTRIC CORPORATION, Tokyo (JP)

(*) Notice: Subject to any disclaimer, the term of this patent is extended or adjusted under 35 U.S.C. 154(b) by 0 days.

(21) Appl. No.: 15/178,694

(22) Filed: Jun. 10, 2016

(65) Prior Publication Data

US 2016/0377565 A1     Dec. 29, 2016

(30) Foreign Application Priority Data

Jun. 25, 2015 (EP) .................................. 15173785

(51) Int. Cl.
  *G01N 27/04* (2006.01)
  *G01N 27/14* (2006.01)
  (Continued)

(52) U.S. Cl.
  CPC ........... *G01N 27/041* (2013.01); *G01N 27/14* (2013.01); *G01R 31/028* (2013.01); *G01N 25/18* (2013.01); *G01N 31/02* (2013.01); *G01R 31/3658* (2013.01)

(58) Field of Classification Search
  CPC ........ G01N 25/00; G01N 25/18; G01N 27/00; G01N 27/02; G01N 27/04; G01N 27/041;
  (Continued)

(56) References Cited

U.S. PATENT DOCUMENTS

| | | | |
|---|---|---|---|
| 6,880,967 B2* | 4/2005 | Isozumi | G01K 3/04 324/548 |
| 8,069,000 B2* | 11/2011 | Kim | G05B 23/0283 363/50 |

(Continued)

FOREIGN PATENT DOCUMENTS

FR     2 768 228 A1     3/1999

OTHER PUBLICATIONS

Kamel et al., "Capacitor Aging Detection for the DC Filters in the Power Electronic Converters using ANFIS Algorithm", Proceeding of the IEEE 28th Canadian Conference on Electrical and Computer Engineering Halifax, Canada, May 3-6, 2015, pp. 663-668.

*Primary Examiner* — Hoai-An D Nguyen
(74) *Attorney, Agent, or Firm* — Birch, Stewart, Kolasch & Birch, LLP

(57) ABSTRACT

A method for on-line monitoring an electrolytic capacitor condition comprising: measuring a voltage ripple across the electrolytic capacitor and the current ripple flowing through the electrolytic capacitor; measuring the temperature of the electrolytic capacitor; emulating the monitored electrolytic capacitor using a capacitor model comprising a capacitor and a solid state adjustable resistor, applying one of the measured ripple to the capacitor model, adjusting the solid state adjustable resistor to minimize the error between an estimated ripple provided by the capacitor model and the other measured ripple not applied to the capacitor model, and estimating an equivalent series resistance of the monitored electrolytic capacitor using value of the solid state adjustable resistor.

12 Claims, 10 Drawing Sheets

(51) Int. Cl.
*G01R 31/02* (2006.01)
*G01N 25/18* (2006.01)
*G01N 31/02* (2006.01)
*G01R 31/36* (2006.01)

(58) Field of Classification Search
CPC ........ G01N 27/14; G01N 27/18; G01N 27/26;
G01N 27/416; G01N 27/42; G01N 31/00;
G01N 31/02; G01R 31/00; G01R 31/02;
G01R 31/028; G01R 31/36; G01R
31/3644; G01R 31/3658
USPC ........ 324/425, 426, 431, 432, 434, 439, 441
See application file for complete search history.

(56) References Cited

U.S. PATENT DOCUMENTS

| | | | |
|---|---|---|---|
| 8,982,591 B2 * | 3/2015 | Avrutsky | G01R 31/028 363/95 |
| 9,397,593 B2 * | 7/2016 | Kato | H02P 6/12 |
| 2010/0026225 A1 * | 2/2010 | Kamei | G05B 9/02 318/471 |
| 2012/0112772 A1 | 5/2012 | Huang | |
| 2012/0153965 A1 | 6/2012 | Huang | |
| 2014/0008998 A1 * | 1/2014 | Schneider | H03K 3/01 307/117 |
| 2015/0205314 A1 * | 7/2015 | Hayashi | G05F 1/56 323/217 |

* cited by examiner

METHOD AND SYSTEM FOR ON-LINE MONITORING ELECTROLYTIC CAPACITOR CONDITION

BACKGROUND OF THE INVENTION

Field of the Invention

The present invention relates generally to a method and system for on-line monitoring an electrolytic capacitor condition.

Description of the Related Art

In the field of Power Electronics, electrolytic capacitors are known as vulnerable components. Their failure leads to out-of-service condition for the entire converter.

Electrolytic capacitors are often the most limiting factor for long-life products. This is why we observe an increased interest in Condition Monitoring technologies, that permit timely replacement of these components, while disturbance on the service rendered by the equipment is minimised.

Solutions have been proposed to detect ageing of electrolytic capacitors. Usually the ageing detection is made by monitoring the variation of some parameters of the electrolytic capacitor. For example, a reduction of the electrolytic capacitance value may be used to detect the end of life of the electrolytic capacitor, an increase of the equivalent series resistance (ESR) may be used to detect the end of life of the electrolytic capacitor or an increase of the loss factor may be used to detect the end of life of the electrolytic capacitor. The estimation of the parameters may be made by using measurements of the capacitor's voltage and current.

Alternatively some methods require in-depth knowledge of the system, like for example an access to gate drive, converters architecture, information from other sensors in order to avoid to use a current sensor, and to determine the current within the electrolytic capacitor using algebraic calculations.

The ESR of an electrolytic capacitor is a good and reliable ageing indicator since it increases relatively strongly during the life of the electrolytic capacitor due to dry-out of the electrolyte.

Operation at high temperature accelerates the degradation of the electrolytic capacitor.

It has been considered that an electrolytic capacitor is considered aged when its ESR value becomes typically between 2 and 3 times the initial ESR value at the same temperature.

SUMMARY OF THE INVENTION

The present invention aims at providing an electrolytic capacitor condition monitoring system which is low cost, resilient to disturbances, has repeatable performance and a sufficient prediction accuracy and which is applicable to a large range of capacitors and operating conditions.

The present invention aims also at providing an on-line monitoring of an electrolytic capacitor condition.

To that end, the present invention concerns a method for monitoring an electrolytic capacitor condition, characterized in that the method comprises:
  measuring a voltage ripple across the electrolytic capacitor and the current ripple flowing through the electrolytic capacitor;
  measuring the temperature of the electrolytic capacitor;
  emulating the monitored electrolytic capacitor using a capacitor model comprising a capacitor and a solid state adjustable resistor;
  applying one of the measured ripple to the capacitor model,
  adjusting the solid state adjustable resistor to minimize the error between an estimate ripple provided by the capacitor model and the other measured ripple not applied to the capacitor model,
  estimating an equivalent series resistance of the monitored electrolytic capacitor using value of the solid state adjustable resistor.

Thus the present invention allows to perform an on-line monitoring of an electrolytic capacitor condition.

On line monitoring allows to determine the condition of an electrolytic capacitor without interrupting the operation a device in which the electrolytic capacitor is included in.

The monitoring method can work with power converters operating at several dozen of kHz without requiring high frequency sampling ADCs or special sampling techniques. This is because the analog pre-processing delivers filtered signal with low frequency contents for analysis by a micro-controller. This naturally provides a good resilience to disturbances which are mostly filtered by an analog processing and also by an algorithm running on the micro-controller.

According to a particular feature, the method comprises further:
  determining an end of life limit value as a function of the temperature of the electrolytic capacitor and an initial equivalent series resistance of the monitored electrolytic capacitor,
  comparing the estimation of the equivalent series resistance of the monitored electrolytic capacitor with the end of life limit value.

Thus, the present invention allows to detect the ageing of the monitored electrolytic capacitor since the equivalent series resistance of the electrolytic capacitor increases and gets closer to the end of life value as the monitored electrolytic capacitor becomes aged.

Furthermore, the electrolytic capacitor condition monitoring is low cost, resilient to disturbances, has repeatable performance and a sufficient prediction accuracy.

The present invention is applicable to a large range of capacitors and operating conditions.

According to a particular feature, a capacitance of the capacitor of the capacitor model is a fixed capacitance value proportional to nominal capacitance of the monitored electrolytic capacitor.

Thus, the present invention is simple to implement and does not require the use of an adjustable capacitor for the capacitor model. The present invention avoids also an initial tuning of the monitoring system to fit with the monitored electrolytic capacitor despite the fact that electrolytic capacitors have usually a relatively large dispersion of their capacitance with respect to nominal value.

According to a particular feature, the method further comprises issuing an alert signal if the estimation of the equivalent series resistance exceeds the end of life limit value.

Thus, the present invention allows to signal that the monitored electrolytic capacitor is reaching end of life and that a maintenance should be performed before the complete failure of the monitored electrolytic capacitor.

The present invention concerns also a system for monitoring an electrolytic capacitor condition, characterized in that the system comprises:
  portion for measuring a voltage ripple across the electrolytic capacitor and the current ripple flowing through the electrolytic capacitor, portion for measuring the temperature of the electrolytic capacitor, portion for emulating the monitored electrolytic capacitor using a capacitor model comprising a capacitor and a solid state adjustable resistor, portion for applying one of the measured ripple to the capacitor model, portion for adjusting the solid state adjustable resistor to minimize the error between an estimate ripple provided by the capacitor model and the other measured ripple not applied to the capacitor model, portion for estimating an equivalent series resistance of the monitored electrolytic capacitor using value of the solid state adjustable resistor.

Thus the present invention allows to perform an on-line monitoring of an electrolytic capacitor condition.

According to a particular feature, the system further comprises:

portion for determining an end of life limit value as a function of the temperature of the electrolytic capacitor and an initial equivalent series resistance of the monitored electrolytic capacitor, portion for comparing the estimation of the equivalent series resistance of the monitored electrolytic capacitor with the end of life limit value.

Thus, the present invention allows to detect the ageing of the monitored electrolytic capacitor since the equivalent series resistance of the electrolytic capacitor increases and gets closer to the end of life value as the monitored electrolytic capacitor becomes aged.

Furthermore, the electrolytic capacitor condition monitoring is low cost, resilient to disturbances, has repeatable performance and a sufficient prediction accuracy.

The present invention is applicable to a large range of capacitors and operating conditions.

According to a particular feature, the system further comprises:

portion for filtering the measured voltage ripple, portion for filtering the measured current ripple.

Thus, the present invention isolates the frequency contents of interest in the measured voltage ripple and current ripple. The relationship between filtered voltage ripple and filtered current ripple can be approximated using a simple model composed of a capacitor in series with a resistor, where the resistive part strongly dominates the impedance of the capacitive part in the range of frequencies of interest.

According to a particular feature, the system further comprises portion for issuing an alert signal if the estimation of the equivalent series resistance exceeds the end of life limit value.

Thus, the present invention allows to signal that the monitored electrolytic capacitor is reaching end of life and that a maintenance should be performed before the complete failure of the monitored electrolytic capacitor.

According to a particular feature, the determination of error between ripple estimation provided by the capacitor model and the other measured ripple not applied to the capacitor model is performed by checking in the time domain if the other measured ripple not applied to the capacitor model is higher than the ripple estimation provided by the capacitor model.

Thus, the present invention allows to determine if the value of estimated ESR must be increased or decreased to be closer to the real value of ESR of the monitored electrolytic capacitor.

Furthermore, this comparison method can be implemented with simple means and is more simple to implement than a frequency based method that would require complex calculations such as FFT.

According to a particular feature, the determination of error between ripple estimation provided by the capacitor model and the other measured ripple not applied to the capacitor model is performed by checking in the time domain if the other measured ripple not applied to the capacitor model is similar to the estimation provided by the capacitor model.

Thus, the present invention allows to determine which value of estimated ESR is the closest to the real value of ESR of the monitored electrolytic capacitor.

Furthermore, this comparison method can be implemented with simple means and is more simple to implement than a frequency based method that would require complex calculations such as FFT.

According to a particular feature, the portion for measuring the current ripple through the electrolytic capacitor is composed of a current sensor which provides a scaled image of the current flowing through the electrolytic capacitor.

The characteristics of the invention will emerge more clearly from a reading of the following description of example embodiments, the said description being produced with reference to the accompanying drawings, among which:

DETAILED DESCRIPTION OF THE PREFERRED EMBODIMENTS

Figure 1:
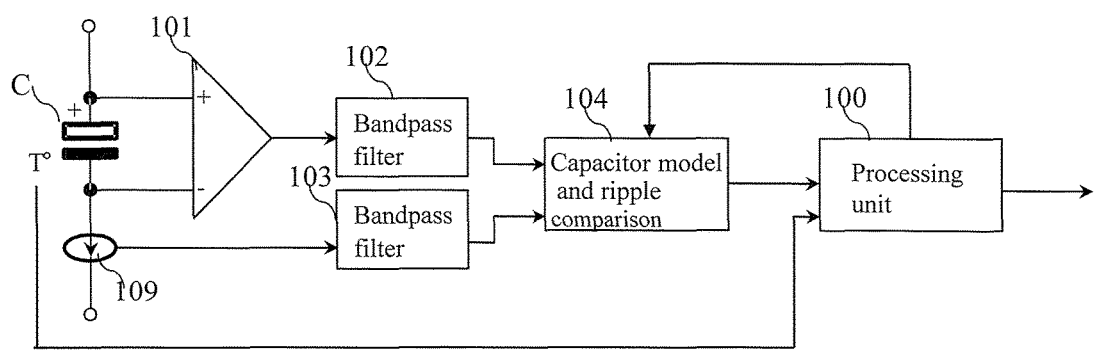
FIG. 1 represents an example of an architecture of an electrolytic capacitor condition monitoring system according to the present invention.

FIG. 1 represents an example of an architecture of an electrolytic capacitor condition monitoring system according to the present invention.

The electrolytic capacitor condition monitoring system monitors the equivalent series resistance of an electrolytic capacitor C.

The electrolytic capacitor condition monitoring system may monitor capacitors having a capacitance value from a few hundred of µF up to a few thousands of µF and a nominal ESR specified around 100 Hz at 20° C. in range of a few dozen of mΩ up to hundreds of mΩ.

The present invention deduces the state of health of the monitored electrolytic capacitor C from the evolution of its ESR value during its lifetime. Based on an initial value of ESR, the present invention determines an end of life value that corresponds to an aged electrolytic capacitor.

The electrolytic capacitor C is considered aged when its ESR parameter has increased significantly with respect to its healthy state, i.e. when the estimated ESR is larger than the end of life value of the ESR, $ESR_{fault}$, derived from the initial value of ESR. Typically the end of life value of the ESR is twice or three times greater than the initial value of ESR.

The initial value of ESR may be determined in several ways: either extracted from datasheets, or deducted from previous measurements. Alternatively, the initial value of ESR may be determined by the electrolytic capacitor condition monitoring system during the first hours, or days of operation.

The adjustment of the end of life value of the ESR with temperature requires the knowledge of the evolution of ESR as a function of temperature, for the type of electrolytic capacitor monitored.

For example, in order to avoid calculations during monitoring operation, the adjustment law is preferably put in a table pre-calculated during an initialization procedure. The initialization of the table may be done several ways.

For example, the table is built using information comprised in the datasheet of the electrolytic capacitor or by using data obtained from pre-characterization of the type of electrolytic capacitor to monitor in order to determine the evolution of the electrolytic capacitor ESR with temperature: ESR=f(T°), considering the ESR in the range of frequency of interest, for example at a frequency value of few dozen of kHz, 10 kHz or 50 kHz for instance.

For example, in order to avoid integrating the errors due to production tolerances, an in-situ method is preferred. The table may be build during the first hours or days of operation of the monitored electrolytic capacitor, by self learning using the present invention. In that case, the ESR is estimated using the present invention, at least one operating temperature point during operation.

A curve fitting method, or an interpolation between the different measures of ESR made at several temperatures can then be used to complete the table with the desired resolution, for example, one value of ESR is stored in the table for each ° C. between 25 and 85° C. Generally, the temperature within the device in which the electrolytic capacitor is included in, varies slowly which enables a reliable estimation of ESR at a given temperature despite the large thermal inertia of the electrolytic capacitor.

The ESR value of the electrolytic capacitor at ambient temperature can easily be estimated following start up operation. Then, after some time, at least another ESR value can be obtained at higher operational temperature. Over a period of a few days, operation at different operating points or at different ambient temperatures may offer new opportunities to estimate values of ESR at other temperatures, thus increasing the accuracy of the fitting. It has to be noted here that the duration of the self-learning period is limited in order to avoid incorporating ESR values that are indicative of capacitor aging and should be exponentially shorter for elevated measured temperatures.

Also the self-learning approach may be used during a calibration procedure performed at factory, using a climatic chamber to control the ambient temperature within the power converter, and thus of its monitored capacitor(s).

Finally, once a value ESR(T) is determined, the corresponding value $ESR_{fault}(T)$ is typically two or three times ESR(T).

When the end of life criterion is reached, an alarm signals that the electrolytic capacitor C has reached its end of life and that a maintenance procedure is required. It has to be noted here that regardless of the end of life criterion is reached, the estimation of ESR is repeating continuously.

The present invention allows individual monitoring of an electrolytic capacitor on a DC bus. Usually, to withstand the high voltage of DC bus or for safety reasons, it is common that two or more electrolytic capacitors are grouped in series forming a string. To reach the required capacitance value for the DC bus, it is also common to group several strings in parallel.

Several electrolytic capacitor condition monitoring systems are used if there are several electrolytic capacitor strings taking into account that the measured ripple current is identical for electrolytic capacitors connected in series and that only one processing unit and one current sensor may be used per string.

The present invention may be non-intrusive if a PCB-based Rogowski coil probe is used. An example of such a current sensor like a PCB-based Rogowski coil is disclosed in the paper of H. L. Votzi, M. Vogelsberger, and H. Ertl, "Low-Cost Current Sensor for Power Capacitors Based on a PCB Rogowski-Coil Rogowski Coil Current Transducer," no. May, pp. 17-19, 2011.

A PCB-based Rogowski coil is particularly well suited for electrolytic capacitors with screw terminals.

For electrolytic capacitors that don't allow the use PCB-based Rogowski coil sensor, the monitoring method can still be non-intrusive by using for instance near-field proximity sensor or PCB-embedded current transformer.

The electrolytic capacitor condition monitoring system comprises an estimator of the ESR. The estimation of the monitored electrolytic capacitor's ESR is performed according to the present invention by adjusting a capacitor's model so as to minimize the error between the measured ripple and the estimated one. The estimated ESR is one parameter of the adjustable capacitor model used.

The capacitor model is advantageously implemented using analogue electronic components and emulates the monitored capacitor in the frequency range of interest, where the impedance of the electrolytic capacitor C is dominated by its ESR value.

The capacitor model comprises a capacitor and a resistor. The resistor of the capacitor model is a solid state adjustable resistor like for example a digitally adjustable resistor or a photosensitive resistor modulated by a LED with an adjustable current source. The solid state adjustable resistor emulates the ESR of the electrolytic capacitor C. The value of the solid state adjustable resistor is proportional to the ESR of the monitored electrolytic capacitor C.

The capacitance of the capacitor of the model is not adjusted and derived from the nominal capacitance of the monitored electrolytic capacitor.

The current that flows in the capacitor model is a scaled image of the current flowing within the monitored electrolytic capacitor.

For example, the capacitor of the capacitor model has a value which is 10000 times lower than the electrolytic capacitor C capacitance value and the value of the solid state adjustable resistor which emulates the ESR of the electrolytic capacitor is 10000 times greater than the ESR of the electrolytic capacitor C.

It has to be noted here that other scaling factors between the capacitor model value and the the electrolytic capacitor C capacitance value may be used according to the present invention.

An ESR in the range of a few tenth of mΩ up to 1Ω implies, according to above mentioned numerical example, using solid state adjustable resistor of 10 kΩ by step of 100 ohm for instance providing then a resolution of 10 mΩ.

Similarly, the capacitor used in the capacitor model has a small value e.g. 100 nF for a 1000 uF monitored electrolytic capacitor C. For example, a class 1 ceramic capacitor, which is stable with temperature, can thus be used for the capacitor model. These are very common and low cost components.

Note that the fixed approximation of monitored electrolytic capacitor C with fixed capacitance has no significant impact on the precision of estimation as its contribution to the estimation of impedance is more significant in very low frequency which is according to the present invention filtered.

The voltage of the electrolytic capacitor C is sensed and scaled by a voltage and scaling sensor 101 and filtered using a bandpass filter 102 in order to remove from the voltage low frequency components. The sensed and filtered voltage named $V_{ripple}$ is provided to a capacitor model and comparison module 104. The voltage of the electrolytic capacitor C is a high DC voltage plus a few volts ripple.

The voltage and scaling sensor 101 may be implemented several ways. In a first way, the voltage and scaling sensor 101 may be implemented for example by performing an attenuation if the electrolytic capacitor condition monitoring system ground is referenced to the negative terminal of the electrolytic capacitor C. In a second way, the voltage and scaling sensor 101 may be implemented for example by performing an attenuation followed by a differential amplification in order to allow high common mode voltage on amplifier's inputs. In a third way, the voltage and scaling sensor 101 may be implemented for example by performing a capacitive coupling using a passive filter in order to remove high DC voltage followed by either an attenuation or a gain depending on ripple amplitude in order to adjust level of ripple in a range compatible with a bandpass filter 102.

In the first and second ways, once the DC component and other low frequency contents is removed, an amplification of ripple may be required.

The current going through the electrolytic capacitor C is sensed by a sensor 109 and filtered using a bandpass filter 103 in order to remove from the sensed current low frequency components. The sensed and filtered current named $I_{ripple}$ is provided to the capacitor model and comparison module 104.

The goal of the amplifying and filtering is to scale and filter the measured current and voltage and then to extract the voltage and current ripples in the frequency band of interest.

The voltage and scaling sensor 101 purpose is to provide a measure in a range of voltage acceptable by the following processing stages. For example, the voltage and scaling sensor 101 performs an attenuation of high voltage capacitor voltage with a resistive divider and the current sensor 109 delivers a low voltage image proportional to the current flowing through the electrolytic capacitor C.

The purpose of the filters 102 and 103 is to isolate the frequency components mostly affected by the ESR while rejecting as much as possible the low frequency disturbances that carry no relevant information for ESR estimation and also high frequencies affected by the inductive region of the capacitor's impedance.

For the electrolytic capacitors, the typical capacitive region extends from DC up to a few kHz, while inductive region due to parasitic series inductance typically starts from a few 100 kHz.

The frequency band of analysis is thus typically located between a few kHz up to 100 kHz. Different topologies can be used to implement the band-pass filters like cascaded high-pass filter with low-pass filter. In practice, it is not required to have a strong attenuation of the high frequency contents.

For example, a first order "low-pass" filter may be used to attenuate these frequencies. For better accuracy of estimation of ESR, a good rejection of low frequency contents is preferred, so at least a second order "high-pass" filter is preferably used like for instance a Sallen & Key filter.

The voltage and current are filtered by the bandpass filters 102 and 103 with similar filters.

If the current sensor 109 modifies the bandwidth in the band of analysis then the bandpass filter 103 is adapted to provide the same bandwidth for the measured current and voltage ripples.

For instance, using a hall effect current sensor with a flat frequency response from DC to 80 kHz and then a first order attenuation above, both high-pass filtering stages for current & voltage would be identical.

No further low pass filtering is required for bandpass filter 103 and a first order low pass filter of the band pass filter 102 may be configured to cut at 80 kHz.

Alternatively, if a pcb-based Rogowski current sensor is used, the high frequency filter for the bandpass filter 103 may be directly handled by the sensor itself.

A temperature sensor noted T° senses the temperature of the electrolytic capacitor C and is provided to a processor 100. As the ESR value of the electrolytic capacitor is dependent of the temperature, the temperature is taken into account according to the present invention.

The electrolytic capacitor condition monitoring system comprises a capacitor model and comparison module 104. The capacitor model and comparison module 104 will be disclosed in more detail in reference to FIG. 2a or 2b. The output of the capacitor model and comparison module 104 is provided to a processing unit 100.

Figure 2A:
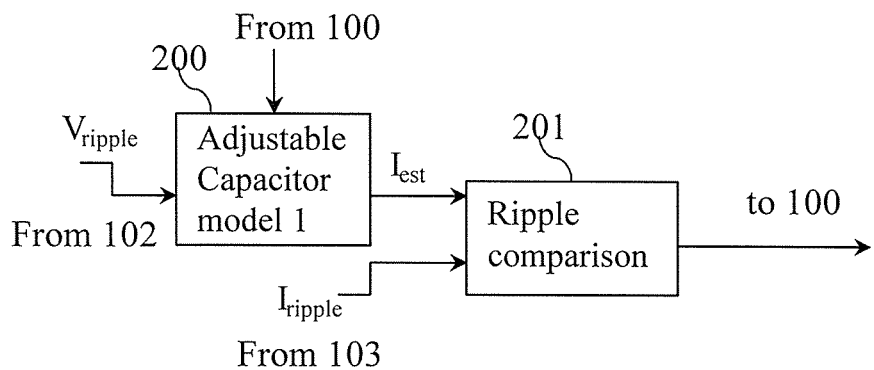
FIG. 2a represents a first example of a capacitor model and comparison module according to a first mode of realization of the present invention.

FIG. 2a represents a first example of a capacitor model and comparison module according to a first mode of realization of the present invention.

According to the first mode of realization of the present invention, the capacitor model and comparison module 104 comprises an adjustable capacitor model 200 and a ripple comparison module 201.

The adjustable capacitor model 200 process the sensed, scaled and filtered voltage $V_{ripple}$ in order to provide an estimated current ripple $I_{est}$ which is provided to a ripple comparison module 201. The adjustable capacitor model 200 receives from the processing unit 100 commands for adjusting the digitally adjustable resistor which emulates the ESR of the electrolytic capacitor. The adjustable capacitor model 200 will be disclosed in more detail in reference to FIG. 3a.

The ripple comparison module 201 compares the estimated current ripple $I_{est}$ to the sensed, scaled and filtered current $I_{ripple}$ and provides a filtered comparison result to the processing unit 100. The ripple comparison module 201 will be disclosed in more detail in reference to FIGS. 4a and 5.

Figure 2B:
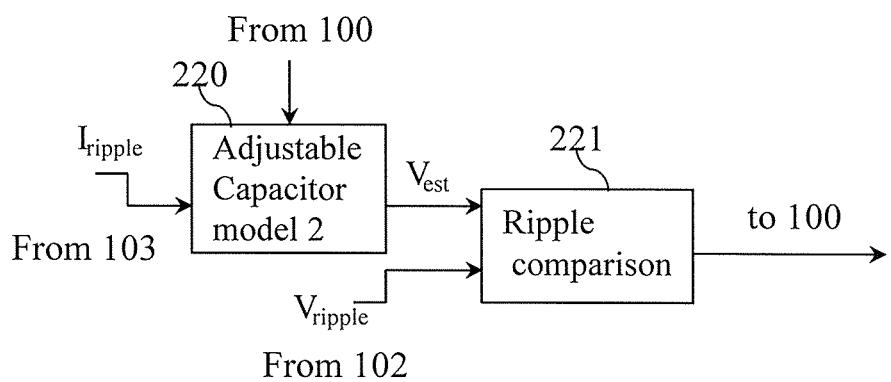
FIG. 2b represents a second example of a capacitor model and comparison module according to a second mode of realization of the present invention.

FIG. 2b represents a second example of a capacitor model and comparison module according to a second mode of realization of the present invention.

According to the second mode of realization of the present invention, the capacitor model and comparison module 104 comprises an adjustable capacitor model 220 and a ripple comparison module 221.

The adjustable capacitor model 220 process the sensed and filtered current $I_{ripple}$ in order to provide an estimated voltage ripple $V_{est}$ which is provided to the ripple comparison module 221. The adjustable capacitor model 220 receives from the processing unit 100 commands for adjusting the digitally adjustable resistor which emulates the ESR of the electrolytic capacitor. The adjustable capacitor model 220 will be disclosed in more detail in reference to FIG. 3b.

The ripple comparison module 221 compares the estimated voltage ripple $V_{est}$ to the the sensed, scaled and filtered voltage $V_{ripple}$ and provides a comparison result to the processor 100. The ripple comparison module 221 will be disclosed in more detail in reference to FIGS. 4b and 5.

Figure 3A:
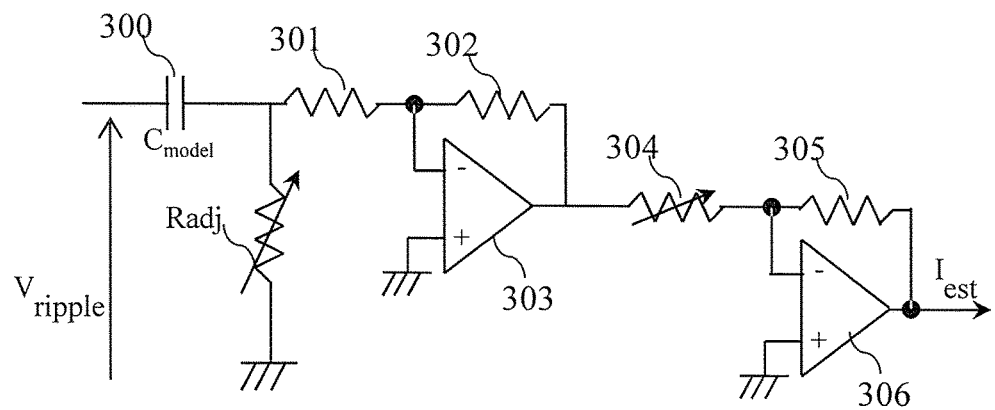
FIG. 3a represents a first example of a capacitor model according to the first mode of realization of the present invention.

FIG. 3a represents a first example of a capacitor model according to the first mode of realization of the present invention.

A first terminal of the capacitor $C_{model}$ of the capacitor model 200 is connected to the input $V_{ripple}$ of the cap or model 200. The second terminal of the capacitor model $C_{model}$ is connected to a first terminal of the digitally adjustable resistor $R_{adj}$ which emulates the ESR of the electrolytic capacitor C and to a resistor 301. The second terminal of the digitally adjustable resistor $R_{adj}$ is connected to the ground. A second terminal of the resistor 301 is connected to the negative input of an amplifier 303 and to a first terminal of a resistor 302.

The positive input of the amplifier 303 is connected to the ground.

A second terminal of the resistor 302 is connected to the output of the amplifier 303 and to a first terminal of an adjustable resistor 304.

$C_{model}$ and $R_{adj}$ constitute a scaled model of the monitored electrolytic capacitor C. Once $R_{adj}$ is correctly adjusted, the ripple current that flows through the digitally adjustable resistor $R_{adj}$ is proportional to the ripple current that flows in the monitored electrolytic capacitor C. Thus, the measure of voltage drop across the digitally adjustable resistor $R_{adj}$ may be used to determine the estimation of ripple current $I_{est}$.

The next two stages composed of components 303 to 306 constitute a non-inverting amplifier with a programmable gain (composed of two cascaded inverting amplifiers) aimed at measuring and scaling the voltage drop that appears across $R_{adj}$.

As an alternative a single stage non inverting amplifier may be used.

The adjustable resistor 304 allows to adjust the gain of the amplifier to obtain an image of the current that flows through the digitally adjustable resistor $R_{adj}$ independently of the value of the digitally adjustable resistor $R_{adj}$.

By adjusting the resistor 304 to have the same value than the digitally adjustable resistor $R_{adj}$ we compensate for the variable nature of $R_{adj}$.

The values of the resistors 302, 301 and 305 define a fixed gain to amplify the current that flows through the digitally adjustable resistor $R_{adj}$ in order to compensate on one hand for the attenuation of the current that flows through the digitally adjustable resistor $R_{adj}$ with respect to the current that flows in monitored electrolytic capacitor C and on the other hand to possibly compensate the gain of the voltage and scaling sensor 101 and the current sensor 109.

A second terminal of the adjustable resistor 304 is connected to the negative input of an amplifier 306 and to a first terminal of a resistor 305.

The positive input of the amplifier 306 is connected to the ground.

A second terminal of the resistor 305 is connected to the output of the amplifier 306.

The output of the amplifier 306 provides the estimated current ripple $I_{est}$.

Figure 3B:
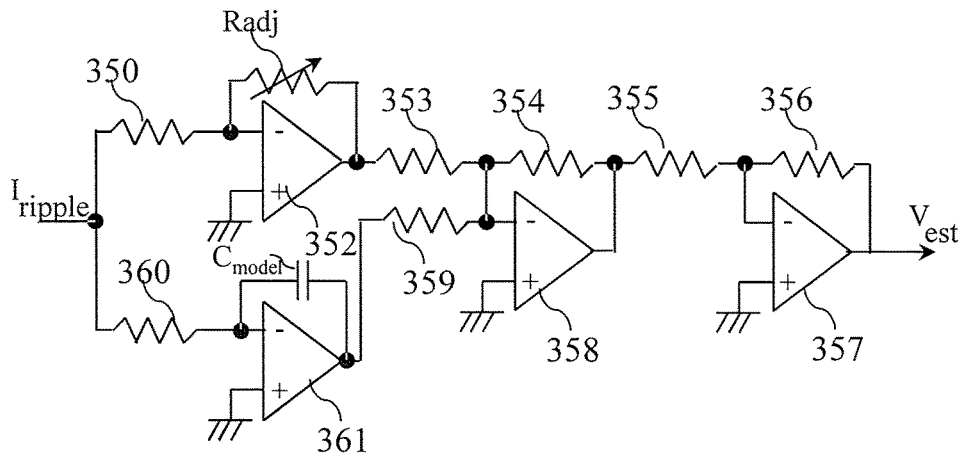
FIG. 3b represents a second example of a capacitor model according to the second mode of realization of the present invention.

FIG. 3b represents a second example of a capacitor model according to the second mode of realization of the present invention.

A first terminal of a resistor 350 is connected to the input of the capacitor model 220. A second terminal of the resistor 350 is connected to the negative input of an amplifier 352 and to a first terminal of an adjustable resistor $R_{adj}$ which emulates the ESR of the electrolytic capacitor.

The positive input of the amplifier 352 is connected to the ground.

A second terminal of the digitally adjustable resistor $R_{adj}$ is connected to the output of the amplifier 352 and to a first terminal of a resistor 353.

A first terminal of a resistor 360 is connected to the input $I_{ripple}$ of the capacitor model 220. A second terminal of the resistor 360 is connected to the negative input of an amplifier 361 and to a first terminal of the capacitor $C_{model}$ of the capacitor model 200.

The positive input of the amplifier 361 is connected to the ground.

A second terminal of the capacitor $C_{model}$ is connected to the output of the amplifier 361 and to a first terminal of a resistor 359. A second terminal of the resistor 359 is connected to the negative input of the amplifier 358, to the second terminal of the resistor 353 and to a first terminal of a resistor 354.

The positive input of the amplifier 358 is connected to the ground.

A second terminal of the resistor 354 is connected to the output of the amplifier 358 and to a first terminal of a resistor 355.

A second terminal of the resistor 355 is connected to the negative input of an amplifier 357 and to a first terminal of a resistor 356.

The positive input of the amplifier 357 is connected to the ground.

A second terminal of the resistor 356 is connected to the output of the amplifier 306.

The output of the amplifier 357 provides the estimated voltage ripple $V_{est}$.

Figure 3C:
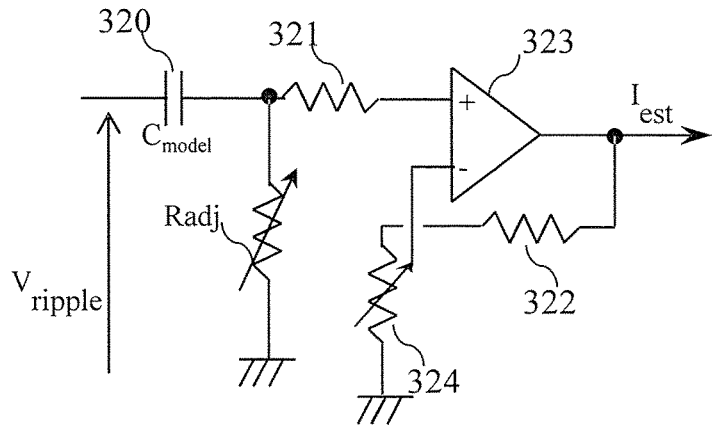
FIG. 3c represents a third example of a capacitor model according to the first mode of realization of the present invention.

FIG. 3c represents a third example of a capacitor model according to the first mode of realization of the present invention.

A first terminal of the capacitor $C_{model}$ of the capacitor model 200 is connected to the input $V_{ripple}$ of the capacitor model 200. The second terminal of the capacitor model $C_{model}$ is connected to a first terminal of the digitally adjustable resistor $R_{adj}$ which emulates the ESR of the electrolytic capacitor C and to a resistor 321. The second terminal of the digitally adjustable resistor $R_{adj}$ is connected to the ground. A second terminal of the resistor 321 is connected to the positive input of an amplifier 323. The resistor 321 may be used for input offset compensation but may be equal to 0 ohm, i.e. replaced by a wire.

The digitally adjustable resistor $R_{adj}$ is implemented using a digitally adjustable potentiometer of which the cursor terminal is connected to one of the two other terminals.

The negative input of the amplifier 323 is connected to the cursor terminal of the digitally adjustable potentiometer 324. The second terminal of digitally adjustable potentiometer 324 is connected to ground. The third terminal of the digitally adjustable potentiometer 324 is connected to one terminal of the resistor 322. The other terminal of the resistor 322 is connected to output of amplifier 323. The resistor 322 may be used to modify the gain of the amplifier 323 but can be equal to null value if not required.

The output of the amplifier 323 provides the estimated ripple $I_{est}$.

The digitally adjustable potentiometer 324 and digitally adjustable resistor $R_{adj}$ are identical components, or possibly parts of the same component if a dual digitally adjustable potentiometer is used. They are programmed similarly so that the impedance between their cursor and their terminal connected to ground are identical for both the digitally adjustable potentiometer 324 and the digitally adjustable resistor $R_{adj}$.

Resistors 321, 322, 324 and the amplifier 323 constitute a non-inverting amplifier, with a variable gain, used to measure and scale the voltage across the digitally adjustable resistor $R_{adj}$.

Figure 3D:
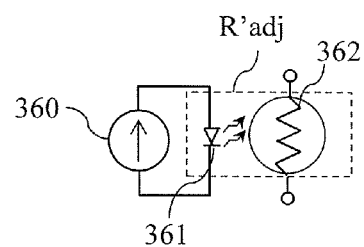
FIG. 3d represents an example of a solid-state adjustable resistor using a photosensitive resistor modulated by a LED with an adjustable current source.

FIG. 3d represents an example of a solid-state adjustable resistor using a photosensitive resistor modulated by a LED with an adjustable current source.

The solid state adjustable resistor $R'_{adj}$ is controlled by an adjustable current source 360 which provides the adjusted current to a Light-Emitting Diode LED 361. The light provided by the LED 361 modifies the resistor value of a photosensitive resistor.

The solid-state adjustable resistor of FIG. 3d also may be a linear optocoupler comprising an integrated circuit that embeds both a LED and a photosensitive transistor.

Figure 3E:
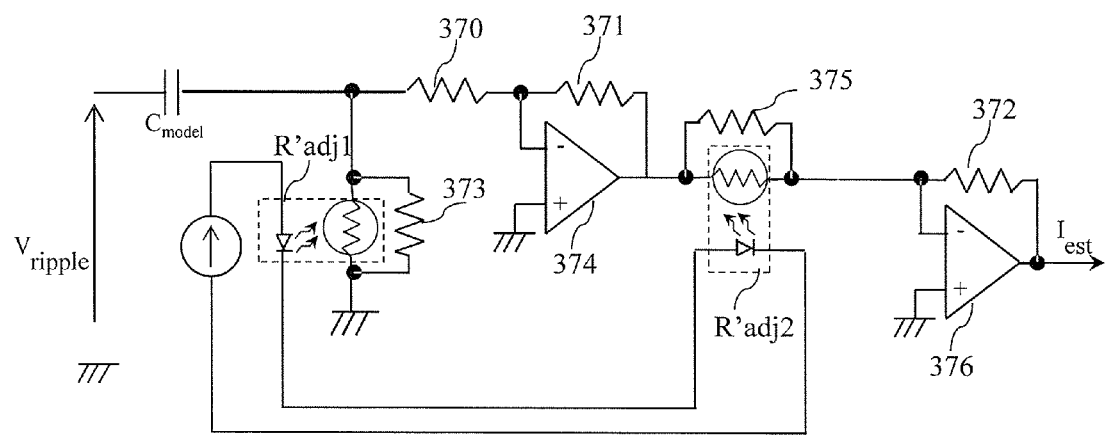
FIG. 3e represents a fourth example of a capacitor model and comparison module according to a first mode of realization of the present invention.

FIG. 3e represents a fourth example of a capacitor model and comparison module according to a first mode of realization of the present invention.

A first terminal of the capacitor $C_{model}$ of the capacitor model 200 is connected to the input $V_{ripple}$ of the cap or model 200. The second terminal of the capacitor model $C_{model}$ is connected to a first terminal of a solid state adjustable resistor $R'_{adj1}$ which emulates the ESR of the electrolytic capacitor C, to a first terminal of a resistor 373 and to a first terminal of a resistor 370. The second terminal of the solid state adjustable resistor $R'_{adj1}$ is connected to a second terminal of a resistor 373 and to the ground. A second terminal of the resistor 370 is connected to the negative input of an amplifier 374 and to a first terminal of a resistor 371.

The positive input of the amplifier 374 is connected to the ground.

A second terminal of the resistor 371 is connected to the output of the amplifier 374, to a first terminal of a resistor 375 and to a first terminal of an adjustable resistor $R'_{adj2}$ that may be a solid state adjustable resistor.

The resistors 373 and 375 have the same value and are used to adjust the maximum value of the equivalent resistances respectively formed by the parallel connection of resistor 373 and $R'_{adj1}$, and by the parallel connection of the resistor 375 and $R'_{adj2}$.

$C_{model}$, $R'_{adj1}$ and the resistor 373 constitute a scaled model of the monitored electrolytic capacitor C. Once the solid state adjustable resistor $R'_{adj1}$ is correctly adjusted, the ripple current that flows in the branch composed of the solid state adjustable resistor $R_{adj1}$ connected in parallel with resistor 373 is proportional to the ripple current that flows in the monitored electrolytic capacitor C. Thus, the measure of voltage drop across the solid state adjustable resistor $R'_{adj1}$ may be used to determine the estimation of ripple current $I_{est}$.

The adjustable resistor $R'_{adj2}$ allows to adjust the gain of the amplifier 376 to obtain an image of the current that flows in the branch composed of the solid state adjustable resistor $R_{adj1}$ connected in parallel with resistor 373, independently of the value of the solid state adjustable resistor $R'_{adj1}$.

By adjusting the resistor $R'_{adj2}$ to have the same value than the solid state adjustable resistor $R'_{adj1}$ the variable nature of $R_{adj1}$ is compensated.

A second terminal of the adjustable resistor $R'_{adj2}$ is connected to the negative input of an amplifier 372, to a second terminal of a resistor 375 and to a first terminal of a resistor 372.

The positive input of the amplifier 376 is connected to the ground.

A second terminal of the resistor 372 is connected to the output of the amplifier 376.

The output of the amplifier 376 provides the estimated current ripple $I_{est}$.

Figure 4A:
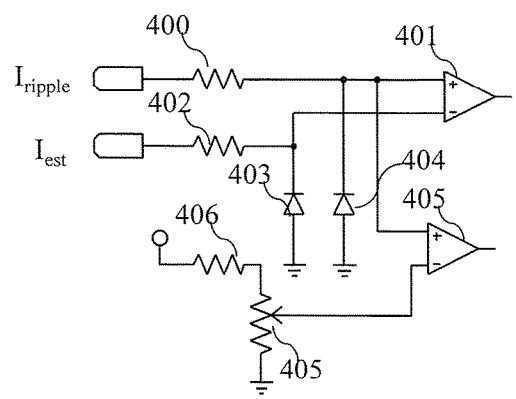
FIG. 4a represents a first example of an analogue part of a comparison module of the electrolytic capacitor condition monitoring system according to the first mode of realization of the present invention.

FIG. 4a represents a first example of an analogue part of a comparison module of the electrolytic capacitor condition monitoring system according to the first mode of realization of the present invention.

The current ripple $I_{ripple}$ is provided to a first input of the ripple comparison module 201 to which a first terminal of a resistor 400 is connected.

A second terminal of the resistor 400 is connected to a positive input of a comparator 401, to a positive input of a comparator 405 and to the cathode of a diode 404.

The estimated current ripple $I_{est}$ is provided to a second input of the ripple comparison module 201 to which a first terminal of a resistor 402 is connected.

A second terminal of the resistor 402 is connected to a negative input of the comparator 401 and to the cathode of a diode 403.

The anodes of the diodes 403 and 404 are connected to the ground.

The negative input of the comparator 405 is connected to a voltage reference composed of a resistor 406 in series with an adjustable resistor 405. The voltage reference defines the level above which the comparison is meaningful, i.e. when current $I_{ripple}$ carries useful information.

Resistor 400 and diode 404 as well as resistor 402 and diode 403 perform a voltage clamp in order to enable comparison of positive parts of signals. Negative voltage at inputs of comparators 401 and 405 does not exceed a diode threshold voltage.

Figure 4B:
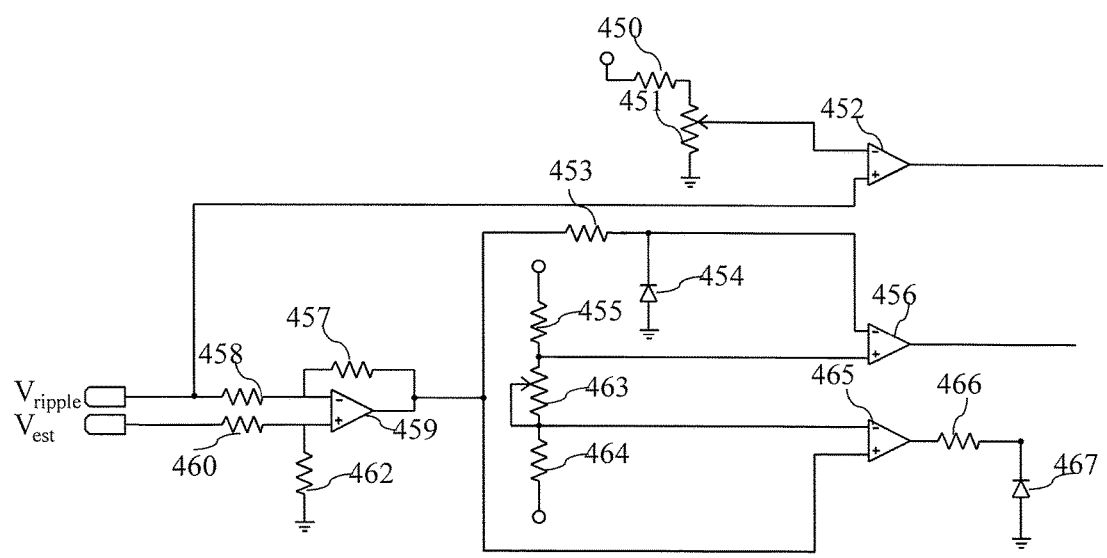
FIG. 4b represents a second example of an analogue part of a comparison module of the electrolytic capacitor condition monitoring system according to the second mode of realization of the present invention.

FIG. 4b represents a second example of an analogue part of a comparison module of the electrolytic capacitor condition monitoring system according to the second mode of realization of the present invention.

The voltage ripple $V_{ripple}$ is provided to a first input of the ripple comparison module 221 to which a first terminal of a resistor 458 and a positive input of a comparator 452 are connected. The comparator 452 is used to generate a signal when $V_{ripple}$ is superior to voltage reference generated by 450, 451 and then to define when comparison can be performed.

A second terminal of the resistor 458 is connected to a negative input of an amplifier 459 and to a first terminal of a resistor 457. The amplifier 459 with surrounding resistors 458, 457, 460, 462 constitute a differential amplifier used to measure the voltage difference between $V_{ripple}$ and estimated voltage ripple $V_{est}$.

The estimated voltage ripple $V_{est}$ is provided to a second input of the ripple comparison module 221 to which a first terminal of a resistor 460 is connected.

A second terminal of the resistor 460 is connected to a positive input of the comparator 459 and to a first terminal of a resistor 462.

The second terminal of the resistor 462 is connected to the ground.

The second terminal of the resistor 457 is connected to the output of the amplifier 459, to a positive input of a comparator 465 and to a first terminal of a resistor 453.

The second terminal of the resistor 453 is connected to the cathode of a diode 454 and to a negative input of a comparator 456.

The anode of the diode 454 is connected to the ground.

A first terminal of a resistor 455 is connected to the positive power supply. A second terminal of the resistor 455 is connected to the positive input of the comparator 456 and to a first terminal of an adjustable resistor 463.

A second terminal of the adjustable resistor 463 is connected to the negative input of the comparator 465 and to a first terminal of a resistor 464.

A second terminal of the resistor 464 is connected to the negative power supply.

The resistive divider composed of resistors 455, 463 and 464 is used to generate two reference voltages, one positive and one negative, for comparison with difference signal delivered by the amplifier 459. The goal is to check if $V_{ripple}$ and $V_{est}$ are similar i.e. if difference between them does not exceed a predetermined value adjusted by resistor 463.

The output of the comparator 465 is connected to a first terminal of a resistor 466.

A second terminal of the resistor 466 is connected to the cathode of a diode 467.

The anode of the diode 467 is connected to the ground.

Figure 5:
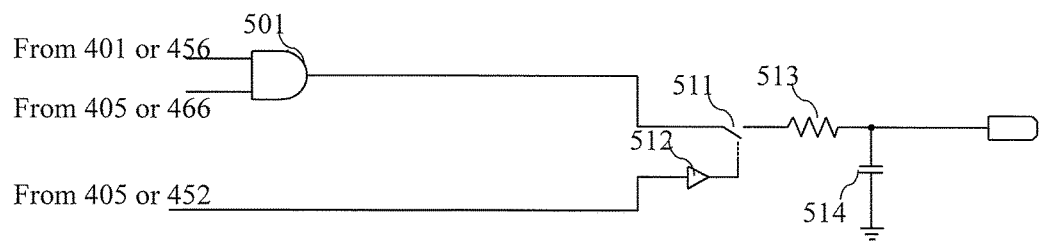
FIG. 5 represents an example of the digital and filtering part of a comparison module of the electrolytic capacitor condition monitoring system according to the first and second modes of realization of the present invention.

FIG. 5 represents an example of the digital and filtering part of a comparison module of the electrolytic capacitor condition monitoring system according to the first and second modes of realization of the present invention.

A first input of the digital and filtering part of the ripple comparison module 201 or 221 receives the signal provided by the comparator 401 or 456 on which is connected a first input of a AND gate 501.

A second input of the digital and filtering part of the ripple comparison module 201 or 221 receives the signal provided by the comparator 405 or the resistor 466 on which is connected a second input of the AND gate 501.

A third input of the digital and filtering part of the ripple comparison module 201 or 221 receives the signal provided by the comparator 405 or 452 on which is connected an input of a buffer 512.

The output of the AND gate 501 is connected to a first terminal of a switch 511. The switch 511 and the buffer 512 represent a three-state buffer.

The output of the buffer 512 controls the switch 511.

The output of the switch 511 is connected to a first terminal of a resistor 513.

A second terminal of the resistor 513 is connected to the processing unit 100, as well as to a first terminal of capacitor 514. The other terminal of 514 is connected to ground.

When the input of the buffer 512 is at logical state '1', i.e. tri-state buffer enabled, the switch 511 is closed and the capacitor 514 either charges or discharges through the resistor 513 depending on logical state of output of the and gate 501. When the input of the buffer 512 is at logical state '0', i.e. tri-state buffer disabled, the switch 511 is open and the charge state of capacitor 514 does not change.

Figure 6:
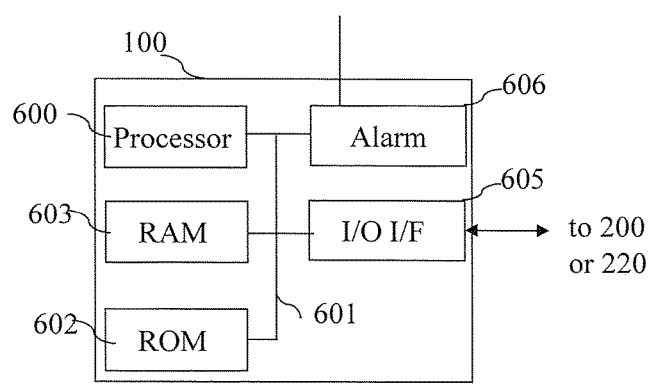
FIG. 6 represents the architecture of a processing unit of the electrolytic capacitor condition monitoring system.

FIG. 6 represents the architecture of a processing unit of the electrolytic capacitor condition monitoring system.

Figure 7:
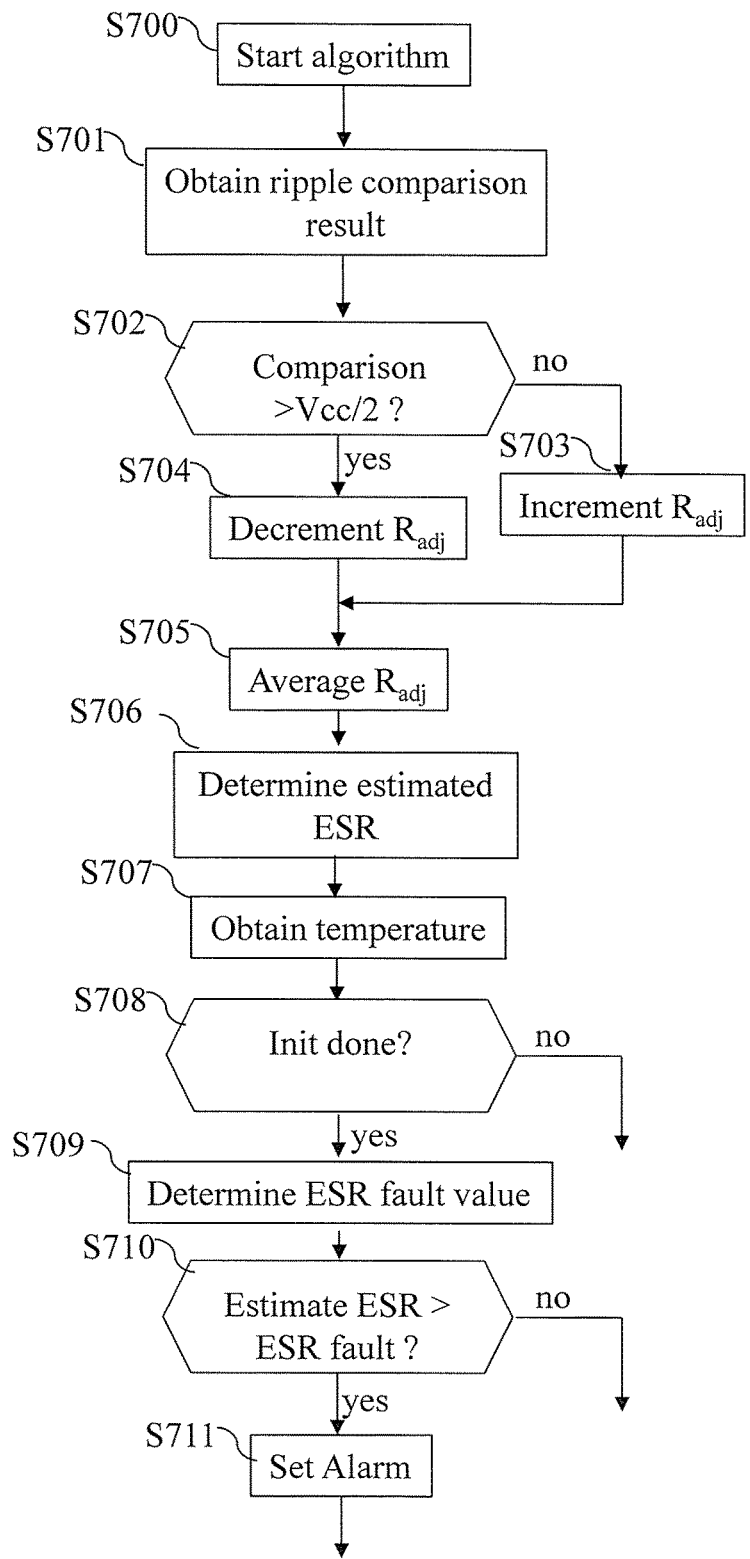
FIG. 7 represents an algorithm for condition monitoring of an electrolytic capacitor according to the first mode of realization of the present invention.
Figure 8:
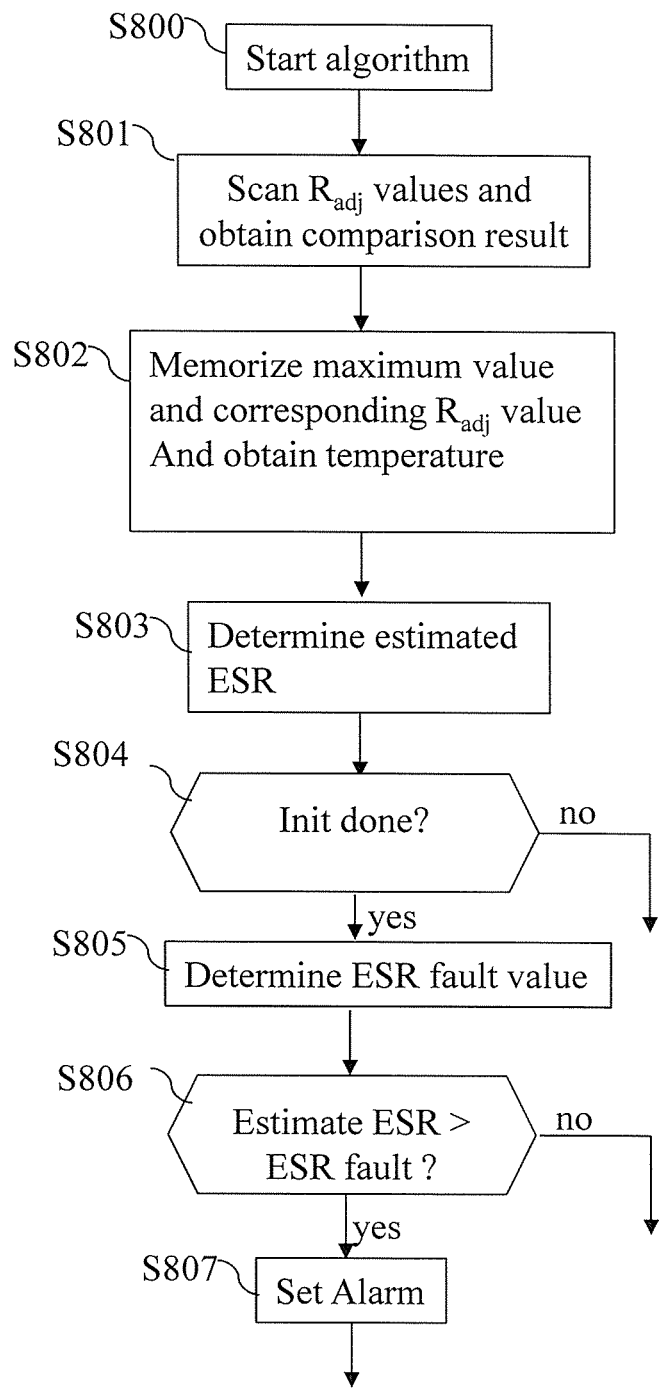
FIG. 8 represents an algorithm for condition monitoring of an electrolytic capacitor according to the second mode of realization of the present invention.

The processing unit 100 has, for example, an architecture based on components connected together by a bus 601 and a processor 600 controlled by a program as disclosed in FIG. 7 or 8.

The bus 601 links the processor 600 to a read only memory ROM 602, a random access memory RAM 603 an input output I/O IF interface 605 and an alarm interface 606. The memory 603 contains registers intended to receive variables and the instructions of the program related to the algorithm as disclosed in FIG. 7 or 8.

The processor 600 receives through the input output I/O IF 605 sensed temperature, output signal from the digital and filtering part that may be analogue or digital and transfers command signals in order to modify the value of the digitally adjustable resistor $R_{adj}$ which emulates the ESR of the electrolytic capacitor.

The processor 600, upon detection of the end of life of the electrolytic capacitor commands the alarm module 606 which is for example a LED or an alarm signal.

The read-only memory, or possibly a Flash memory 602 contains instructions of the programs related to the algorithm as disclosed in FIG. 7 or 8, when the processing unit 100 is powered on, to the random access memory 603.

The processing unit 100 may be implemented in software by execution of a set of instructions or program by a programmable computing machine, such as a PC (Personal Computer), a DSP (Digital Signal Processor) or a microcontroller; or else implemented in hardware by a machine or a dedicated component, such as an FPGA (Field-Programmable Gate Array) or an ASIC (Application-Specific Integrated Circuit).

In other words, the processing unit 100 includes circuitry, or a device including circuitry, causing the processing unit 100 to perform the program related to the algorithm as disclosed in FIG. 7 or 8.

FIG. 7 represents an algorithm for condition monitoring of an electrolytic capacitor according to the first mode of realization of the present invention.

More precisely, the present algorithm is executed by the processor 600 of the processing unit.

The present algorithm is, for example, executed periodically on a minute or hour or day, periodicity. An internal timer of the processor 600, or a timer emulated by software, can be used to determine when it is time to execute the present algorithm. The present algorithm may also be executed at any time, when an estimation of ESR is required.

At step S700, the present algorithm starts.

At next step S701, the processor 600 obtains the comparison result from the ripple comparison module 201.

At next step S702, the processor 600 checks if the comparison result obtained at step S701 is upper than Vcc/2, where Vcc is the voltage level of the logic power supply. Note that Vcc/2 is the average voltage between electrical levels corresponding to logic level '0' and logic level '1'.

If the comparison result obtained at step S701 is upper than Vcc/2, the processor 600 moves to step S704 and decrements the value of the solid state adjustable resistor which emulates the ESR of the electrolytic capacitor. After that, the processor 600 moves to step S705.

If the comparison result obtained at step S701 is not upper than Vcc/2, the processor 600 moves to step S703 and increments the value of the solid state adjustable resistor which emulates the ESR of the electrolytic capacitor. After that, the processor 600 moves to step S705.

At next step S705 an averaging of successive values of the solid state adjustable resistor is performed by considering the current value of the solid state adjustable resistor, determined at steps S703 or S704 with a previous predetermined number of values determined at previous executions of the present algorithm.

At next step S706, the processor 600 estimates the ESR of the electrolytic capacitor using the average value of the solid state adjustable resistor.

A next step S707, the processor 600 obtains the temperature from the sensor T°. Since it is not possible to measure the internal temperature of the electrolytic capacitor, a measure of the case temperature is used instead. For example, the temperature sensor is a thermistor, a thermocouple or an integrated temperature sensor glued to the electrolytic capacitor's package for instance.

At next step S708, the processor 600 checks if the initialization procedure is finished or not. If the initialization procedure is already finished, the processor 600 moves to step S709, otherwise the temperature value T and the estimated ESR at that temperature are returned to the initialization procedure in order to construct a table of different end of life values of the ESR $ESR_{fault}$ as a function of temperature.

At next step S709, the processor 600 determines the end of life ESR value as function of temperature obtained at step S707. The value $ESR_{fault}$ is advantageously determined by using the pre-calculated value determined during the initialization procedure.

The electrolytic capacitor is considered aged when its ESR parameter has increased significantly with respect to its healthy state, i.e. when the estimated ESR is upper than the end-of-life value of the ESR derived from the initial value of ESR. Typically the end of life value of the ESR is twice or three times greater than the initial value of ESR.

The initial value of ESR may be determined in several ways: either extracted from datasheets, or deducted from previous measurements. Alternatively, the initial value of ESR may be determined by the electrolytic capacitor condition monitoring system during the first hours, or days of operation.

At next step S710, the processor 600 checks if the estimation of the ESR of the electrolytic capacitor is upper than the end of life ESR value.

If the estimation of the ESR of the electrolytic capacitor is upper than the end of life ESR value, the processor 600 moves to step S710. Otherwise, the processor 600 interrupts the present algorithm.

At step S710, the processor 600 commands the transfer of an alarm signal that indicates that the electrolytic capacitor has reach its end of life and that a maintenance procedure is required.

FIG. 8 represents an algorithm for condition monitoring of an electrolytic capacitor according to the second mode of realization of the present invention.

More precisely, the present algorithm is executed by the processor 600 of the processing unit.

The present algorithm is executed, for example, periodically on a minute or hour or day, periodicity.

At step S800, the present algorithm starts.

At next step S801, the processor 600 transfers different values to the solid state adjustable resistor which emulates the ESR of the electrolytic capacitor and obtains for each transferred value, the result of the comparison from the ripple comparison module 221.

At next step S802, the processor 600 memorizes the value of the solid state adjustable resistor which corresponds to the maximum value of results of the comparisons if the maximum value is upper than a previously stored value.

It has to be noted here that both steps S801 and S802 may be combined. In that case, only the value of the solid state adjustable resistor that corresponds to maximum value of result is memorized. Temperature is also be measured at that step. The processor 600 obtains the temperature from the sensor T°.

Since it is not possible to measure the internal temperature of the electrolytic capacitor, a measure of the case temperature is used instead. For example, the temperature sensor is a thermistor, a thermocouple or an integrated temperature sensor glued to the electrolytic capacitor's package for instance.

At next step S803, the processor 600 estimates the ESR of the electrolytic capacitor using the value of the digitally adjustable resistor $R_{adj}$ stored.

At next step S804, the processor 600 checks if the initialization procedure is finished or not. If it has been done, the execution continues to step S805, otherwise the temperature value determined at step S802 and the estimated ESR determined at step S803 are returned to the initialization procedure in order to construct a table of different $ESR_{fault}$ values as a function of temperature.

At next step S805, the processor 600 determines the end of life ESR value, $ESR_{fault}$, for the temperature determined at step S802.

The electrolytic capacitor is considered aged when its ESR parameter has increased significantly with respect to its healthy state, i.e. when the estimated ESR is upper than the end of life value of the ESR derived from the initial value of ESR. Typically the end of life value of the ESR is twice or three times greater than the initial value of ESR.

The initial value of ESR may be determined in several ways: either extracted from datasheets, or deducted from previous measurements. Alternatively, the initial value of ESR may be determined by the electrolytic capacitor condition monitoring system during the first hours, or days of operation.

At next step S806, the processor 600 checks if the estimation of the ESR of the electrolytic capacitor is upper than the end of life ESR value.

If the estimation of the ESR of the electrolytic capacitor is upper than the end of life ESR value, the processor 600 moves to step S807. Otherwise, the processor 600 interrupts the present algorithm.

At step S807, the processor 600 commands the transfer of an alarm signal that indicates that the electrolytic capacitor has reach its end of life and that a maintenance procedure is required.

Figure 9:
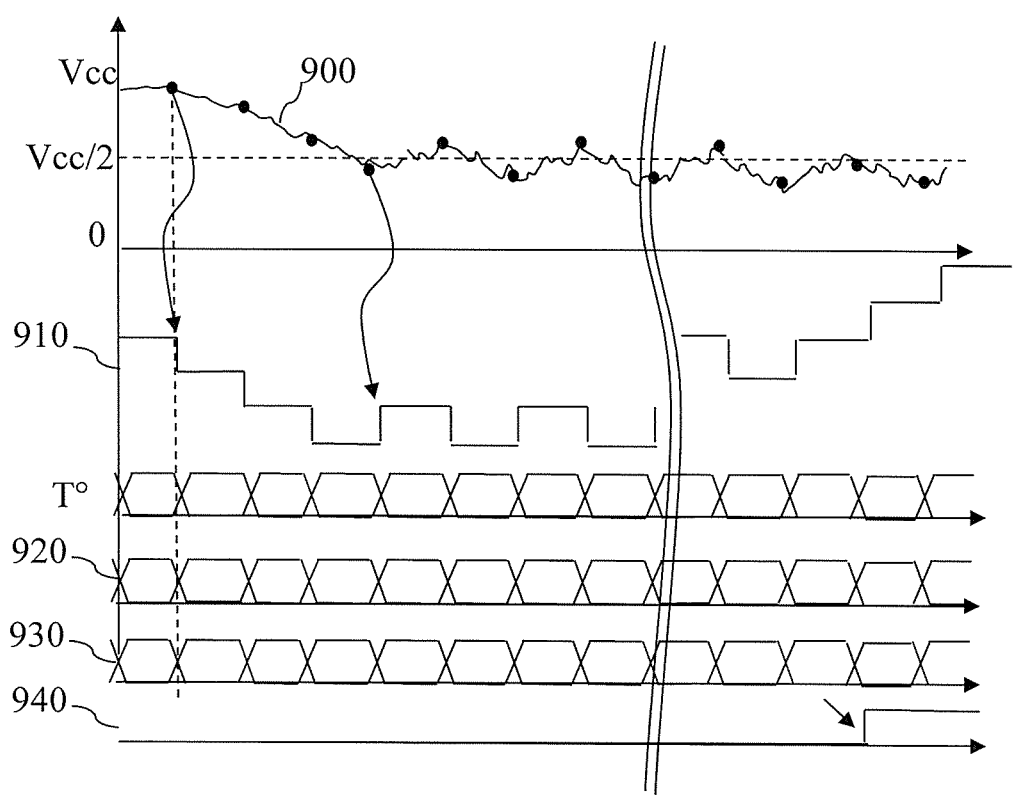
FIG. 9 represents curves and chronograms of signals provided by the present invention in order to monitor the electrolytic capacitor condition.

FIG. 9 represents curves and chronograms of signals provided by the present invention in order to monitor the electrolytic capacitor condition.

The curve noted 900 represents the comparison result obtained from the ripple comparison module 201.

Each dot represents the value considered for decision, an increase or a decrease of the solid state adjustable resistor value.

The curve noted 910 represents the different values taken by the digitally adjustable resistor $R_{adj}$ which emulates the ESR of the electrolytic capacitor.

The curve noted T° represents the different values of temperature.

The curve noted 920 represents an example wherein the end of life value of the ESR is adjusted with respect to current temperature.

The curve noted 930 represents the estimation of the ESR and the curve noted 940 represents the alarm signal which is set to high level if the estimation of the ESR of the electrolytic capacitor is upper than the end of life ESR value.

The curves noted T°, 920 and 930 are numerical values updated every evaluation of the monitoring algorithm.

Figure 10:
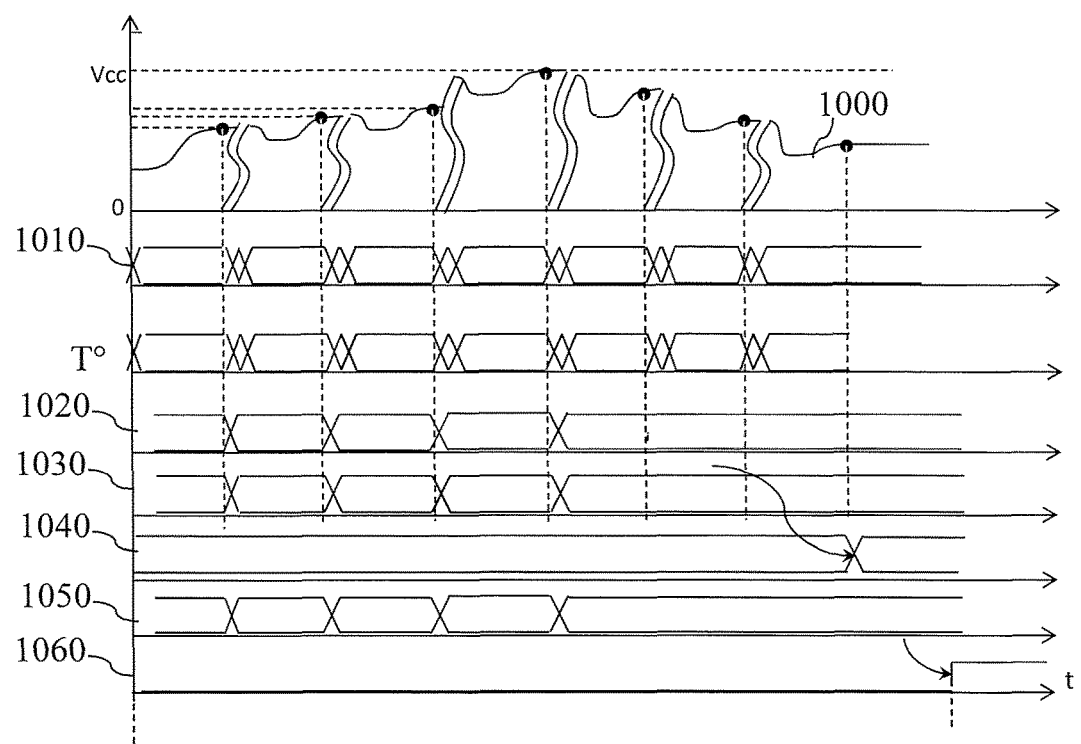
FIG. 10 represents curves and chronograms of signals provided by the present invention in order to monitor the electrolytic capacitor condition.

FIG. 10 represents curves and chronograms of signals provided by the present invention in order to monitor the electrolytic capacitor condition.

The curve noted 1000 represents the comparison result obtained from the ripple comparison module 221.

The curve noted 1010 represents the different values taken by the solid state adjustable resistor which emulates the ESR of the electrolytic capacitor.

The curve noted T° represents the different values of temperature.

The curve noted 1020 represents the value of the solid state adjustable resistor which are stored and updated only each time a new maximum is found.

The curve noted 1030 represents the different memorized values of temperature and updated only each time a new maximum is found.

The curve noted 1040 represents the memorized end of life values of the ESR $ESR_{fault}$ as function of the temperature memorized.

The curve noted 1050 represents the memorized estimation of the ESR and the curve noted 1060 represents the alarm signal which has a high level if the estimation of the ESR of the electrolytic capacitor is upper than the end of life ESR value.

The curves noted 1010, T°, 1020, 1030, 1040 and 1050 are numerical values updated every evaluation of the monitoring algorithm.

Naturally, many modifications can be made to the embodiments of the invention described above without departing from the scope of the present invention.

What is claimed is:

1. A method for on-line monitoring an electrolytic capacitor condition, comprising:
    measuring a voltage ripple across the electrolytic capacitor and the current ripple flowing through the electrolytic capacitor,
    measuring the temperature of the electrolytic capacitor,
    emulating the monitored electrolytic capacitor using a capacitor model comprising a capacitor and a solid state adjustable resistor,
    applying one of the measured ripple to the capacitor model,
    adjusting the solid state adjustable resistor to minimize the error between an estimated ripple provided by the capacitor model and the other measured ripple not applied to the capacitor model,
    estimating an equivalent series resistance of the monitored electrolytic capacitor using value of the solid state adjustable resistor.

2. The method according to claim 1, wherein the method comprises further:
    determining an end of life limit value as a function of the temperature of the electrolytic capacitor and an initial equivalent series resistance of the monitored electrolytic capacitor,
    comparing the estimation of the equivalent series resistance of the monitored electrolytic capacitor with the end of life limit value.

3. The method according to claim 2, wherein a capacitance of the capacitor of the capacitor model is a fixed capacitance value proportional to nominal capacitance of the monitored electrolytic capacitor.

4. The method according to claim 2, wherein the method further comprises issuing an alert signal if the estimation of the equivalent series resistance exceeds the end of life limit value.

5. A system for monitoring an electrolytic capacitor condition, comprising:
    portion for measuring a voltage ripple across the electrolytic capacitor and the current ripple flowing through the electrolytic capacitor,
    portion for measuring the temperature of the electrolytic capacitor,
    portion for emulating the monitored electrolytic capacitor using a capacitor model comprising a capacitor and a solid state adjustable resistor,
    portion for applying one of the measured ripple to the capacitor model,
    portion for adjusting the solid state adjustable resistor to minimize the error between an estimate ripple provided by the capacitor model and the other measured ripple not applied to the capacitor model,
    portion for estimating an equivalent series resistance of the monitored electrolytic capacitor using value of the solid state adjustable resistor.

6. The system according to claim 5, wherein the system further comprises:
    portion for determining an end of life limit value as a function of the temperature of the electrolytic capacitor and an initial equivalent series resistance of the monitored electrolytic capacitor,
    portion for comparing the estimation of the equivalent series resistance of the monitored electrolytic capacitor with the end of life limit value.

7. The system according to claim 6, wherein the system further comprises:
    portion for filtering the measured voltage ripple,
    portion for filtering the measured current ripple.

8. The system according to claim 6, wherein a capacitance of the capacitor of the capacitor model is a fixed capacitance value proportional to nominal capacitance of the monitored electrolytic capacitor.

9. The system according to claim 6, wherein the system further comprises portion for issuing an alert signal if the estimation of the equivalent series resistance exceeds the end of life limit value.

10. The system according to claim 5, wherein the determination of error between ripple estimation provided by the capacitor model and the other measured ripple not applied to the capacitor model is performed by checking in the time domain if the other measured ripple not applied to the capacitor model is higher than the ripple estimation provided by the capacitor model.

11. The system according to claim 5, wherein the determination of error between ripple estimation provided by the capacitor model and the other measured ripple not applied to the capacitor model is performed by checking in the time domain if the other measured ripple not applied to the capacitor model is similar to the estimation provided by the capacitor model.

12. The system according to claim 6, wherein the portion for measuring the current ripple through the electrolytic capacitor is composed of a current sensor which provides a scaled image of the current flowing through the electrolytic capacitor.

* * * * *